United States Patent [19]
Hawkins et al.

[11] Patent Number: 6,029,089
[45] Date of Patent: Feb. 22, 2000

[54] LEAD RETENTION AND SEALING SYSTEM

[75] Inventors: Rodney Hawkins, Marina Del Rey; Scott Gibson, Granada Hills; Buehl E. Truex, Glendora, all of Calif.

[73] Assignee: Pacesetter, Inc., Sylmar, Calif.

[21] Appl. No.: 09/113,874

[22] Filed: Jul. 10, 1998

[51] Int. Cl.[7] .................................................. A61N 1/375
[52] U.S. Cl. ............................ 607/37; 439/909; 439/271
[58] Field of Search ...................... 607/37, 36; 439/909, 439/271, 278, 283, 775, 272, 273

[56] References Cited

U.S. PATENT DOCUMENTS

| | | |
|---|---|---|
| Re. 31,058 | 10/1982 | Povejsil . |
| 4,166,628 | 9/1979 | Blaydon . |
| 4,259,962 | 4/1981 | Peers-Trevarton . |
| 4,262,982 | 4/1981 | Kenny ....................................... 607/37 |
| 4,469,104 | 9/1984 | Peers-Trevarton ....................... 607/37 |
| 4,932,409 | 6/1990 | Hirschberg . |
| 4,934,366 | 6/1990 | Truex et al. . |
| 4,942,876 | 7/1990 | Gotthardt . |
| 4,954,105 | 9/1990 | Fischer . |
| 5,324,312 | 6/1994 | Stokes et al. . |
| 5,433,734 | 7/1995 | Stokes et al. . |

*Primary Examiner*—Kennedy J. Schaetzle

[57] ABSTRACT

A lead retention and sealing system for an implantable medical device comprises a lead receiving channel with an open end for slidably receiving a connecting end of an electrical lead and a closed end not open to an inner sealed portion of the medical device. The connecting end of the lead does not break the seal of the medical device. The receiving channel includes an electrical contact electrically connected with circuitry hermetically sealed within the medical device for mating contact with a respective portion of the lead when moved to a connecting position. A flexible seal mounted in the receiving channel sealingly engages the outer peripheral surface of the lead and retains the lead at the connecting position. It is so shaped that insertion of the lead into the receiving channel requires less force than its removal from the channel and includes an annular ring member extending toward the longitudinal axis of the channel from an outer annular base to an inner annular lip for initial engagement with the electrical lead as the lead is moved toward the connecting position. The inner annular lip is closer to the closed end of the receiving channel than the outer annular base. The flexible seal preferably lies in a plane of revolution angled approximately 45° with respect to the longitudinal axis of the channel. The inner annular lip is juxtaposed with the annular tip end of a ring seal on the lead and upon attempted withdrawal of the lead opposes such withdrawal.

11 Claims, 3 Drawing Sheets

LEAD RETENTION AND SEALING SYSTEM

FIELD OF THE INVENTION

The present invention relates generally to an implantable medical device, such as a pacemaker, and its connection with an implantable electrical lead to the electrical circuits within a hermetically sealed housing of the medical device. More particularly, the present invention relates to a sealing system that retains and seals the electrical lead in place inside a connector top of the medical device while isolating the electrical contacts of the lead and of the connector top from body fluids.

BACKGROUND OF THE INVENTION

Pacemakers and other implantable devices such as cardiac defibrillators require a method of passing electrical signals between the device and the heart. To transmit these signals from the device to the heart, implantable electrical leads are used. The leads make electrical contact with the device through the connector top ring and tip contacts. The signals are then transmitted from the device to the heart via the implantable leads. To ensure an uninterrupted electrical path between the device and the heart, a strong reliable mating between the implantable leads and the connector top of the device is necessary. It is also desirable to seal the entrance of the connector top of the device from body fluids. To achieve these connector conditions, external calibrated torque wrenches are used to secure the leads in place by means of set screws or by compressing an active seal. The use of external tools for achieving connector conditions has created reliability problems (cored septum, stripped wrench, hex, and the like). Further, time is required to insure electrical contact while the tool is being used.

Modern pacemakers monitor the activity of a heart and provide a stimulation pulse in the absence of normal heart activity. Advantageously, such devices are relatively small, light-weight and implantable. In order to sense and stimulate the heart, however, such pacemakers must be used with a pacemaker lead—an electrical conductor that carries electrical signals between the heart and the pacemaker. Advantageously, the pacemaker lead can be inserted into the heart transvenously through a relatively simple and well-known surgical procedure. Disadvantageously, one end of the lead (designated herein as the "connecting end") must be electrically and mechanically secured to the pacemaker in a way that provides for a long-term safe and secure, yet detachable, connection. Those skilled in the pacemaker art have long sought for a simple, yet reliable and safe, means for making this detachable electrical and mechanical connection between the pacemaker device and the connecting end of the pacemaker lead.

In order to appreciate the advantages of the present invention, it will help first to have a basic understanding of the manner in which the mechanical and electrical connection functions are carried out in prior art pacemakers. The main components associated with the connection function of known prior art pacemakers are shown in FIGS. 1 and 2. A pacemaker 10 electrically includes a battery 14 that powers electrical circuits 12. The pacemaker electrical circuits 12 and battery 14 are mechanically housed and hermetically sealed in a suitable housing 16. Typically, this housing or case 16 is shaped to include a flat side or platform 20 to which a suitable epoxy connector 22 can be bonded. At least one feed through terminal 18, in electrical contact with the electrical circuits 12, passes through the case or housing 16 and protrudes out from the platform 20. This feed through terminal 18 is electrically isolated from the case 16. A platinum wire 24, or other suitable conductive element, connects the terminal 18 to a conductive connector block 26 that is fitted within the connector 22. A pacemaker lead 28, having a proximal electrode 30, connects to the pacemaker electrical circuits by inserting the proximal electrode 30 into a receiving channel 31 of the connector 22 until the electrode 30 is in contact with the connector block 26. A set screw 32 is then securely tightened using a torque wrench 34 to firmly hold the electrode 30 in both mechanical and electrical connection with the connector block 26. A septum (not shown) is typically placed over the set screw 32 in order to prevent body fluids from seeping through the set screw hole. Further, sealing ribs or rings 36 on the connecting end of the pacemaker lead are designed to tightly engage the inside edges of the receiving channel 31 in order to prevent any body fluids from entering into the receiving channel 31 once the connecting end of the lead has been pushed into the connector 22.

Representative descriptions of many of the features and functions of prior art pacemaker connection systems may be found in U.S. Pat. Nos. 5,433,734 and 5,324,312 to Stokes et al.; U.S. Pat. No. 4,942,876 to Gotthardt; U.S. Pat. No. 4,934,366 to Truex et al.; U.S. Pat. No. 4,932,409 to Hirschberg; and U.S. Pat. No. 4,259,962 to Peers-Trevarton. Most notable of these, for purposes of the present invention, is the patent to Truex et al., in which a feedthrough connector for an implantable medical device combines the connector function with the feedthrough function and eliminates the need for the cast epoxy connector previously used on such devices. The feedthrough connector includes a barrel assembly having open and closed ends. The open end of the assembly has an opening for receiving a slidably inserted electrical lead. The barrel assembly includes cylindrical metal, conductive portions separated by cylindrical ceramic insulating portions. Spring contacts are mounted on the inside of the metal portions and are adapted to make mechanical and electrical contact with the appropriate contacts of an electrical lead when the lead is inserted into the connector. The outer side of the metal portions are electrically connected to the appropriate electrical circuit within the housing, and the open end of the barrel assembly is welded to the device housing so that the inside of the device can be hermetically sealed. Releasable lead gripping means are included as part of the barrel assembly to detachably lock and seal the electrical lead in its inserted position inside of the connector.

While that which is described in these prior patents varies greatly relative to, for example, different types of locking mechanisms for performing the mechanical connection function, or different types of arrangements for performing the electrical feedthrough function, including the use of bipolar or multiple connector leads, all such systems include the use of a premolded or cast connector 22 that is bonded to a sealed pacemaker housing 16 in which the electrical circuits are located.

Typically, known connectors 22 are cast in place from epoxy to the platform or header 20 of the pacemaker, or a premolded connector is bonded to the platform 20 using a suitable sealing and bonding agent. Further, once the electrical connection is made from the terminal post 18 to the connector block 26, and the connector is attached to the housing, all remaining voids within the connector 22, not including the receiving channel 31 into which the proximal end of the lead is to be inserted, must be filled with a suitable filler material, such as a two-component epoxy or silicone rubber.

It was with knowledge of the foregoing state of the technology that the present invention has been conceived and is now reduced to practice.

SUMMARY OF THE INVENTION

The present invention relates to a lead retention and sealing system for an implantable medical device which comprises a lead receiving channel with an open end for slidably receiving a connecting end of an electrical lead and a closed end not open to an inner is hermetically sealed portion of the medical device. The connecting end of the lead does not break the hermetically sealed portion of the medical device. The receiving channel includes an electrical contact electrically connected with circuitry hermetically sealed within the medical device for mating contact with a respective portion of the lead when moved to a connecting position. A flexible seal mounted in the receiving channel sealingly engages the outer peripheral surface of the lead and retains the lead at the connecting position. It is so shaped that insertion of the lead into the receiving channel requires less force than its removal from the channel and includes an annular ring member extending toward the longitudinal axis of the channel from an outer annular base to an inner annular lip for initial engagement with the electrical lead as the lead is moved toward the connecting position. The inner annular lip is closer to the closed end of the receiving channel than the outer annular base. The flexible seal preferably lies in a plane of revolution angled approximately 45° with respect to the longitudinal axis of the channel. The inner annular lip is juxtaposed with the annular tip end of a ring seal on the lead and upon attempted withdrawal of the lead opposes such withdrawal.

In short, the invention comprises a passive seal which acts to both retain the lead and isolate the electrical contacts from bodily fluids. The main characteristics of the seal are:
- a flexible inner ring that prevents internal body fluids from entering the connector's cavity bore once the implantable lead is inserted; and
- a 45° undercut which allows for the deflection of the above mentioned ring in addition to securing the lead in place. The seal is shaped such that insertion of the lead requires less force than the removal of the lead.

Once the lead is inserted into the connector top's cavity bore, the flexible ring of the seal expands around the silicone boot of the lead. This action seals the entrance of the connector bore and isolates the device from body fluids.

Once the implantable lead is in place, the passive seal retains the lead in position by means of lead seals resistance. Once the lead is inserted, its ring seals tend to fall back closing the bore opening thus providing additional fluid isolation capabilities. On the other hand, the passive seals flexible ring expands forward towards the lead's ring seals.

This particular seal movement allows for the retention of the lead. The gap between the lead ring seals and the passive seal is very small. Therefore a slight pull-out of the lead from the connector top will cause the seals to interfere. It is this interference that creates the retention force which keeps the lead from losing electrical contact with the device.

The electrical contacts are laid out such that when the lead is retained, electrical contact is ensured by geometry and relative position.

In order to remove the lead from the device, the lead ring seals need to overcome the resistance of the passive seal and squeeze under the expanded ring.

A primary feature, then, of the present invention is the provision of an implantable medical device, such as a pacemaker, and its associated implantable electrical lead with a sealing system that secures the electrical lead in place inside a connector top of the medical device while isolating the electrical contacts of the lead and of the connector top from body fluids.

Another feature of the present invention is the provision of an implantable medical device with a connector top that requires no external tool to activate, thereby eliminating associated problems.

Still another feature of the present invention is the provision of such an implantable medical device with a passive seal which allows for immediate electrical contact upon lead insertion.

Yet another feature of the present invention is the provision of such an implantable medical device with a passive seal that will secure the lead in place inside the connector top.

Still a further feature of the present invention is the provision of such an implantable medical device with a passive seal which isolates the electrical contacts of the connector top from bodily fluids.

Still a further feature of the present invention is the provision of such an implantable medical device for which no external tool is required to secure the electrical lead in place, eliminating associated problems.

Still a further feature of the present invention is the provision of such an implantable medical device with which immediate electrical contact is achieved upon lead insertion.

Yet a further feature of the present invention is the provision of such an implantable medical device with a simple one time lead insertion procedure to initiate electrical contact, body fluid sealing, and lead retention.

Still another feature of the present invention is the provision of such an implantable medical device with fewer parts resulting in reduction in cost.

Still another feature of the present invention is the provision of such an implantable medical device with a completely hermetically sealed connector top.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
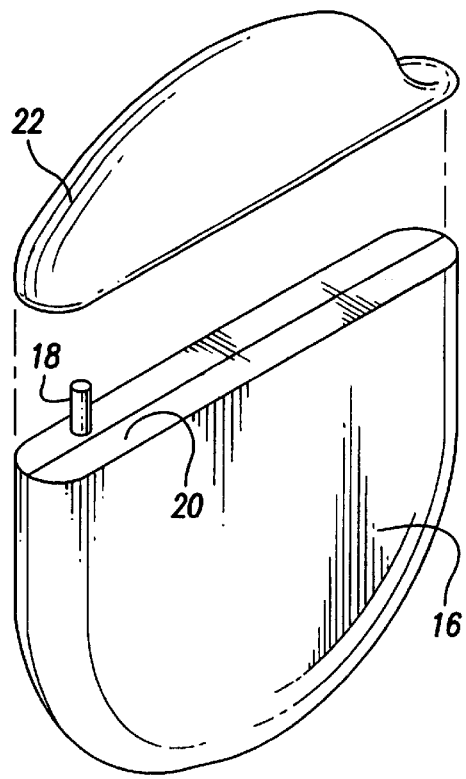
FIG. 1 is an exploded perspective view of a prior art pacemaker showing the sealed pacemaker housing and its cast epoxy connector top.
Figure 2:
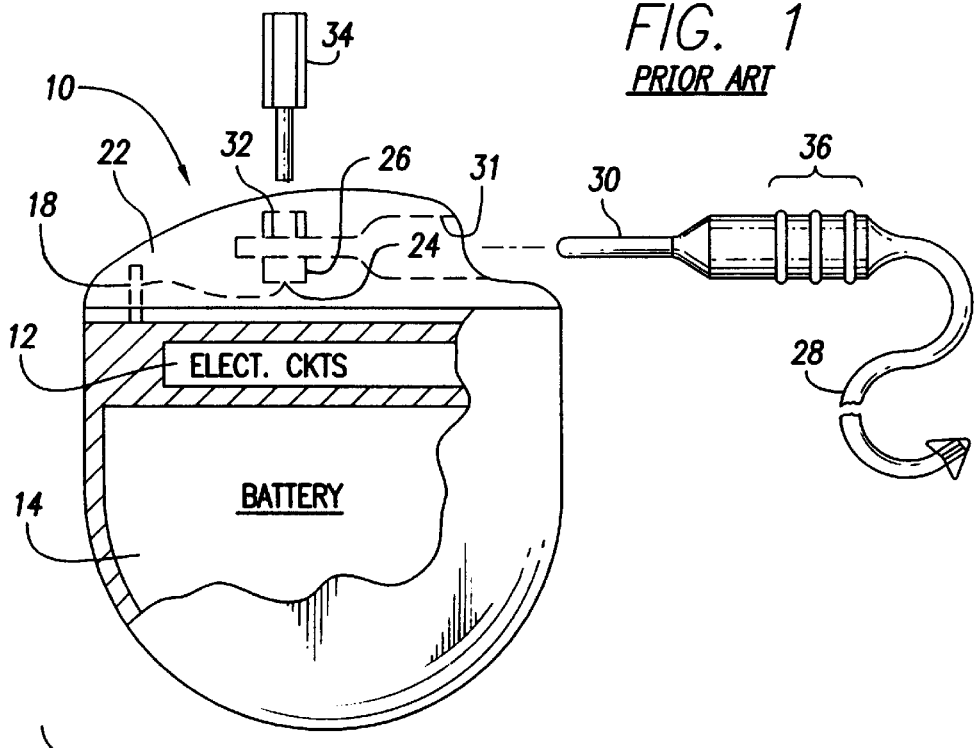
FIG. 2 is a partially cutaway side view of a prior art pacemaker, showing the assembled relationship among the main components thereof.
Figure 3:
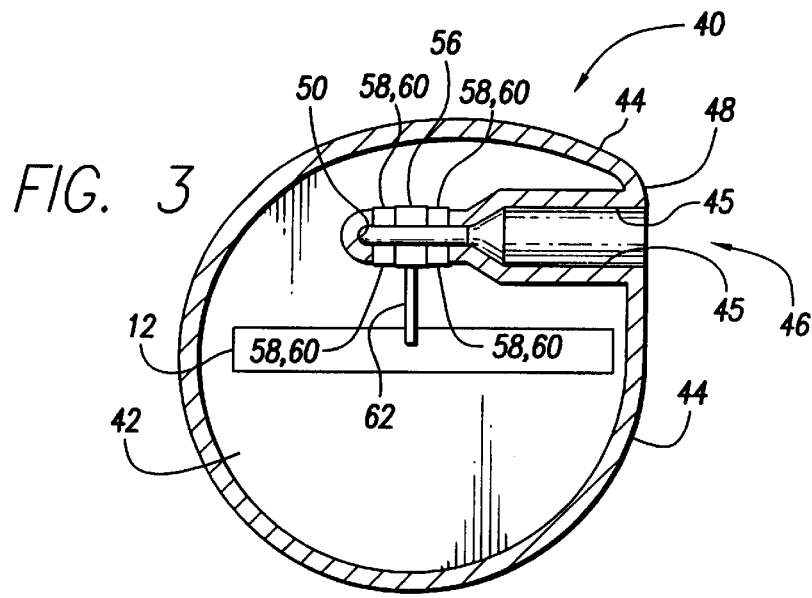
FIG. 3 is a side elevational view in section conceptionally illustrating the layout and hermetically sealed area of a pacemaker embodying the present invention.

Turn again to the drawings and now to FIG. 3, which should be compared to FIG. 2. FIG. 3 depicts a simplified side sectional view of a pacemaker 40 incorporating the present invention. In FIG. 3, that portion of the pacemaker that is hermetically sealed is the shaded area 42. This area is enclosed by the case 44 of the pacemaker. As with the prior art device, this sealed area 42 includes the electrical circuits 12 of the pacer. Unlike the prior art device, a receiving channel 46 protrudes inwardly into the pacer. This channel may conceptually be thought of as an indented channel for it includes an open end 48 flush with the surface of the pacer housing 44 and a closed end 50 within the pacer housing 44, thereby forming, as it were, a long narrow indent within the pacer housing 44. As will be described more fully below, the receiving channel 46 is not formed by indenting the pacer housing 44. Nonetheless, for purposes of illustrating those areas of the pacer that are hermetically sealed from those areas that are not, it may be helpful to conceptualize the receiving channel as an indented channel. The inside walls 45 of the receiving channel 46 are not included within the hermetically sealed areas of the pacemaker 40 for they are open to the outside environment of the pacer through the open end 48. In contrast, the reverse side of the inside walls 45 of the receiving channel 46 (referred to hereafter as the "backside" or "outside" walls of the receiving channel 46) are exposed to the hermetically sealed inner portions of the pacemaker.

Figure 4:
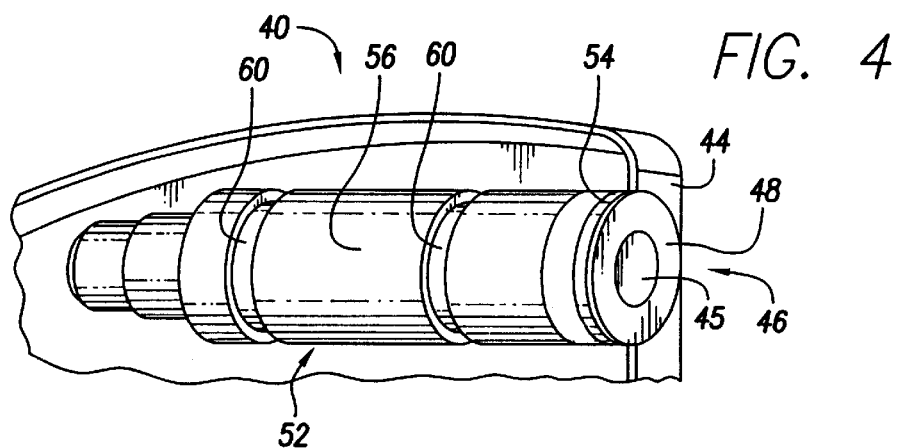
FIG. 4 is a detail perspective view illustrating a connector bore unit employed by the pacemaker of FIG. 3.
Figure 5:
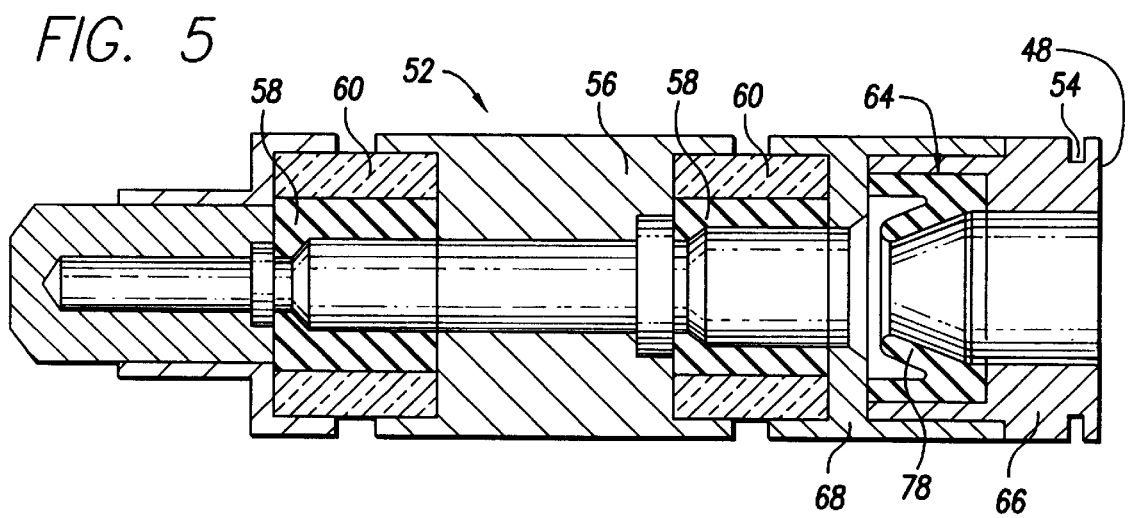
FIG. 5 is a detail side elevational view in section employing the unique sealing construction of FIGS. 6 AND 7 are, respectively, detail side elevational views illustrating a portion of the connector bore unit illustrated in FIG. 5 and an electrical lead about to be connected thereto (FIG. 6) and fully connected therewith (FIG. 7)

Still referring to FIG. 3, but turning additionally to FIGS. 4 AND 5, the receiving channel 46 is actually defined by a generally cylindrical connector bore unit 52. The connector bore unit 52 is integrally formed with an annular groove 54 adjacent its open end 48 which engages with a suitably shaped portion of the case 44 for mounting on the case. Firm attachment is preferably achieved by welding. A portion 56 of the walls of the connector bore unit 52 are made from a conductive material such as titanium. This conductive portion is insulated from the pacer case 44 by insulating (nonconductive) portions 58 of the walls of the connector bore unit 52 which are adjacent the conductive portion. Typically, these nonconductive portions 58 may be made from short ceramic tubular sections that are hermetically bonded to the conductive portion 56 and the remaining metallic portions of the connector bore unit 52 as by glass 60 which is applied molten, then solidified. However, any suitable nonconductive material, such as an epoxy or polymer substance, could be used to perform this insulating function providing that a suitable hermetic bond is created.

The backside or outside of the conductive portion 56 is electrically connected to the pacemaker circuits 12 by means of a suitable electrical conductor 62. Advantageously, because the conductor 62 is only included within the sealed portion 42 of the pacer, it can be made from any suitable electrically conductive material, not just those types of conductors (such as titanium) that are compatible with exposure to body fluids. However, the conductor 62 should be made from a material that is compatible with the type of material used for the conductive portion 56 of the connector bore unit 52 in order to prevent any galvanic or other adverse reactions between dissimilar metals in electrical contact with each other.

Figure 6:
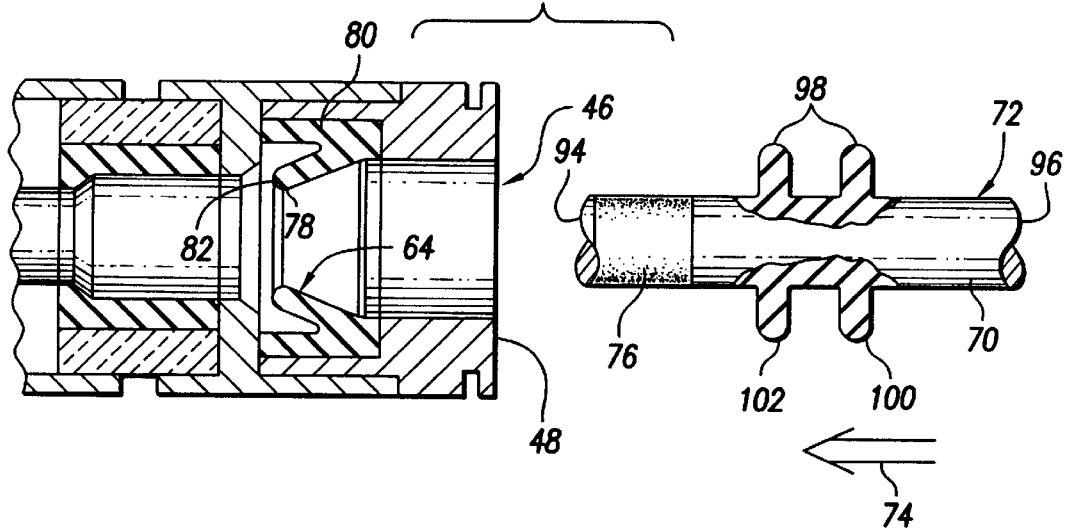

As seen in FIG. 5 and in still greater detail in FIGS. 6 AND 7, the connector bore unit 52 is provided with a sealing system embodying the invention which will now be described. To this end, a flexible ring lock seal 64 is provided which may be molded in position between a titanium seal housing 66 abutting another titanium member 68 which, in turn, abuts the insulating portion 58. The ring lock seal 64 is thereby present in the receiving channel 46 positioned to sealingly engage the outer peripheral surface 70 of an electrical lead 72 which is to be inserted into the receiving channel in the direction indicated by an arrow 74. In customary fashion, the electrical lead 72 includes a ring contact 76 which slidably engages with a spring contact located within the conductive portion 56 when it is inserted fully into the receiving channel 46 (see FIG. 7).

Figure 7:
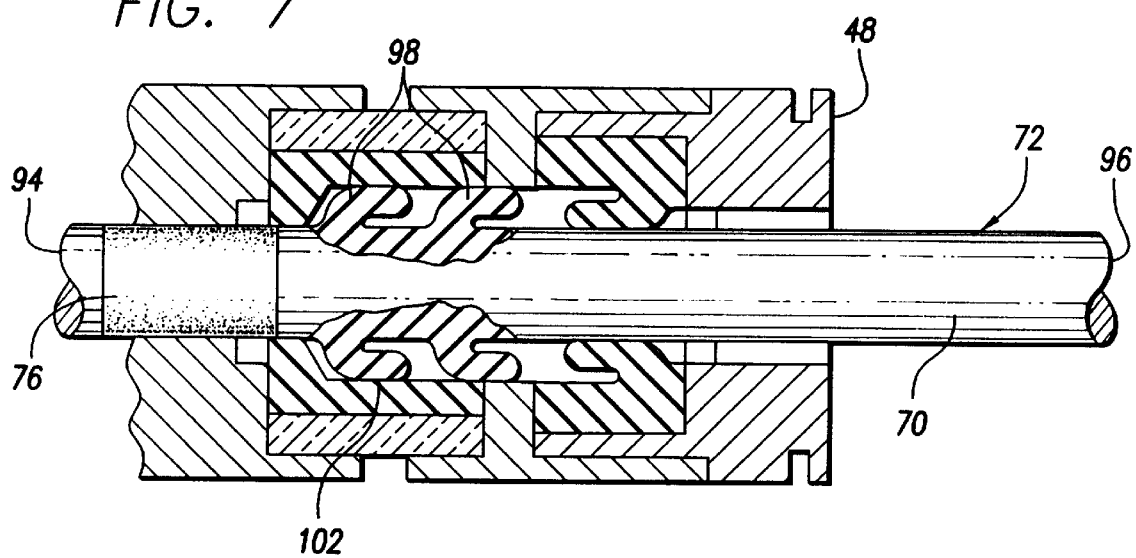
Figure 8:
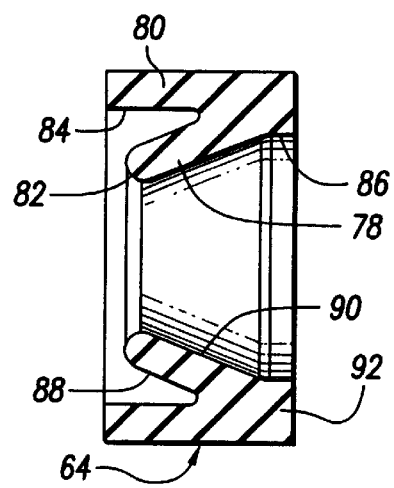
FIG. 8 is a detail side elevational view illustrating the ring lock seal of the invention.

Viewing especially FIG. 8, the ring lock seal 64 includes an annular ring member 78 which extends toward the longitudinal axis of the receiving channel 46 from an outer annular base 80 mounted in the receiving channel as earlier described to an inner annular lip 82 for initial engagement with the electrical lead 72 as the electrical lead is moved toward the connecting position. For this to occur, the inner diameter of the annular ring member 78 at its annular lip 82 must be substantially less than the outer diameter of the electrical lead 72 at its peripheral surface 70. When the electrical lead reaches the connecting position as indicated in FIG. 7, the inner annular lip 82 generally faces the closed end 50 (FIG. 3) of the receiving channel. The ring lock seal 64 thereby prevents the passage of fluid into the receiving channel 46 once the electrical lead is "in place" and it also serves to retain the electrical lead at the connecting position.

Additionally, the ring lock seal 64 is shaped such that insertion of the electrical lead into the receiving channel 46 requires less force than removal of the electrical lead from the receiving channel. In a first instance, this results solely from the construction of the ring lock seal. Specifically, the annular base 80 of the ring lock seal 64 includes first and second inner peripheral surfaces, 84, 86, respectively. The first inner peripheral surface 84 is nearer the closed end of the receiving channel than the second peripheral surface 86 and the annular ring member 78 projects inwardly toward the longitudinal axis of the receiving channel 46 from a location longitudinally intermediate the first and second inner peripheral surfaces. The first inner peripheral surface 84 has an inner extent, or diameter, which is greater than that of the second inner peripheral surface 86, the latter being sufficiently large to allow the sliding reception of the electrical lead 72. In a preferred construction, the annular ring member 78 lies in a plane of revolution which is angled approximately 45° with respect to the longitudinal axis of the receiving channel which defines an undercut region 88.

When the electrical lead 72 is inserted into the receiving channel 46, and approaches or actually reaches the connecting position, an inner surface 90 of the annular ring member 78 actually moves into engagement with the outer peripheral surface 70 of the lead and the undercut region 88 is moved toward the inner peripheral surface 84. When an attempt is made to withdraw the electrical lead from the receiving channel 46, the withdrawal force is imparted from the lead to the annular ring member 78 by reason of their frictional engagement. This force is then transmitted from the base of the annular ring member to the heavier material region 92 of the annular base 80 effectively counteracting the attempt to withdraw the lead. Of course, if sufficient force is imparted to the electrical lead 72, it can be withdrawn. This would cause the annular ring member 78 to reverse its position illustrated in FIG. 7 so that the annular lip 82 faces the open end 48 rather than the closed end 50 and with the undercut region 88 actually engaging the outer peripheral surface 70 of the electrical lead.

It was earlier stated tha this ring lock seal 64 is shaped such that insertion of the electrical lead into the receiving channel 46 requires less force than removal of the electrical lead from the receiving channel, and a first such instance was presented in the preceding paragraph. In a second instance, this results from the interaction of the ring lock seal 64 and the electrical lead 72. More specifically, consider that the electrical lead 72 includes a forward end 94, an aft end 96, and as illustrated in FIGS. 6 and 7, a pair of flexible lead ring seals 98 projecting outwardly circumferentially from the outer peripheral surface 70 intermediate the forward and aft ends 94, 96 to an annular tip end 100. Each lead ring seal 98 is of a dimension out to the annular tip 100 end greater than that of the receiving channel 46 such that upon insertion of the electrical lead into the receiving channel and engagement of the lead ring seal by the inner peripheral surface of the open channel, the lead ring seal is caused to fold against the outer peripheral surface 70 of the electrical lead 72 such that the annular tip end 100 faces toward the aft end, that is, toward the open end 48 of the connector bore unit 52.

As the electrical lead 72 is inserted into the receiving channel 46, outer surfaces 102 of the lead ring seals 98 slide engageably across the inner surface 90 of the annular ring member 78 and when they pass beyond the annular ring member, slide across, then come to rest on, the inner peripheral surface of the receiving channel 46, specifically, the insulating portion 58, viewing FIG. 7. When this occurs, the inner annular lip 82 of the annular ring member 78 is generally aligned, juxtaposed, with the annular tip ends 100 of the ring seals and engageable with the annular tip end of the closest lead ring seal. This construction also opposes withdrawal of the electrical lead from the receiving channel 46 although, as previously stated, if sufficient force is imparted to the electrical lead 72, it can be withdrawn. This would cause the lead ring seals 98 to reverse their positions as illustrated in FIG. 7 so that their tip ends 100 face the forward end of the lead 72 and the closed end 50 of the receiving channel 50. In turn, the friction of the lead ring seals 98 against the ring lock seal 64 would drag the annular ring member 78 until the lip 82 faces the open end 48 rather than the closed end 50 and with the undercut region 88 actually engaging the outer peripheral surface 70 of the electrical lead.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A lead retention and sealing system for an implantable medical device for receiving an electrical lead, the lead retention and sealing system comprising:

lead receiving means for slidably receiving a connecting end of the electrical lead having an outer peripheral surface, the lead receiving means defining a receiving channel within the medical device, the receiving channel having a longitudinal axis and an open end for receiving the electrical lead, and a closed end that is not open to an inner sealed portion of the medical device, the connecting end of the electrical lead being slidably received within the receiving channel without breaking into the sealed portion of the medical device, the receiving channel including at least one electrical contact being electrically connected with circuitry hermetically sealed within the medical device for mating contact with a respective portion of the electrical lead when moved to a connecting position; and flexible seal means in the receiving channel positioned to sealingly engage the outer peripheral surface of the electrical lead and for retaining the electrical lead at the connecting position, the seal means having an undercut region to enable deflection of the flexible seal means such that insertion of the electrical lead into the receiving channel requires less force than removal of the electrical lead therefrom.

2. The lead retention and sealing system, as set forth in claim 1, wherein the seal means includes:

an annular ring member extending toward the longitudinal axis from an outer annular base mounted in the receiving channel to an inner annular lip for initial engagement with the electrical lead as the electrical lead is moved toward the connecting position, the inner annular lip generally facing the closed end of the receiving channel and configured to deflect toward the undercut region during initial engagement with the electrical lead.

3. The lead retention and sealing system, as set forth in claim 2, wherein the flexible seal means lies in a plane of revolution which is angled approximately 45° with respect to the longitudinal axis.

4. The lead retention and sealing system, as set forth in claim 2, wherein the base includes first and second inner peripheral surfaces, the first inner peripheral surface being nearer the closed end of the receiving channel than the second peripheral surface, the flexible seal means projecting inwardly toward the longitudinal axis from a location intermediate the first and second inner peripheral surfaces, the first inner peripheral surface having an inner extent which is greater than that of the second inner peripheral surface and wherein the area between the inner annular lip and the first inner peripheral surface defines the undercut region.

5. A lead retention and sealing system for an implantable medical device comprising:

an electrical lead having an outer peripheral surface and a connecting end with an electrical contact thereon;

lead receiving means for slidably receiving the connecting end of the electrical lead, the lead receiving means defining a receiving channel within the medical device, the receiving channel having an inner peripheral surface and a longitudinal axis and an open end for receiving the electrical lead, and a closed end that is not open to an inner sealed portion of the medical device, the connecting end of the electrical lead being slidably received within the receiving channel without breaking into the seal of the medical device, the receiving channel including at least one electrical contact for being electrically connected with circuitry hermetically sealed within the medical device for mating contact with a respective portion of the electrical lead when moved to a connecting position; and flexible seal means in the receiving channel positioned to sealingly engage the outer peripheral surface of the electrical lead and for retaining the electrical lead at the connecting position, the seal means having an undercut portion to enable deflection of the flexible seal means such that insertion of the electrical lead into the receiving channel requires less force than removal of the electrical lead therefrom.

6. The lead retention and sealing system, as set forth in claim 5, wherein the electrical lead includes a forward end, an aft end, and at least one flexible lead ring seal projecting outwardly circumferentially from the outer peripheral surface thereof intermediate the forward and aft ends to an annular tip end, said lead ring seal having a circumference greater than that of the receiving channel such that upon insertion of the electrical lead into the receiving channel and engagement of the ring seal by the inner peripheral surface of the open channel, the ring seal is caused to fold against the outer peripheral surface of the electrical lead such that the annular tip end faces toward the aft end; and wherein the seal means includes an annular ring member extending toward the longitudinal axis from an annular base mounted in the receiving channel to an inner annular lip for initial engagement with the electrical lead as the electrical lead is moved toward the connecting position, the inner annular lip generally facing the closed end of the receiving channel and defining the undercut region between the inner annular lip toward the closed end of the receiving channel, the inner annular lip being generally aligned with the annular tip end of the ring seal and engageable therewith and opposing withdrawal of the electrical lead from the lead receiving means.

7. The lead retention and sealing system, as set forth in claim 6, wherein the flexible seal means lies in a plane of revolution which is angled approximately 45° with respect to the longitudinal axis.

8. The lead retention and sealing system, as set forth in claim 6, wherein the base includes first and second inner peripheral base surfaces, the first inner peripheral base surface being nearer the closed end of the receiving channel than the second inner peripheral base surface, the flexible seal means projecting inwardly toward the longitudinal axis from a location intermediate the first and second inner peripheral base surfaces, the first inner peripheral base surface having an inner extent which is greater than that of the second inner peripheral base surface and wherein the area between the inner annular lip and the first inner peripheral base surface defines the undercut region.

9. A lead retention and sealing apparatus suitable for retaining an electrical lead in a receiving channel of an implantable medical device wherein the receiving channel has a longitudinal axis, a closed end, and an open end for receiving the electrical lead, the lead retention and sealing apparatus comprising:

a flexible annular ring member extending toward the longitudinal axis from an annular base mounted in the receiving channel to an inner annular lip for initial engagement with the electrical lead as the electrical lead is moved toward a connecting position; and wherein the inner annular lip generally faces the closed end of the receiving channel and is configured to deflect outward from the longitudinal axis toward an undercut region during initial engagement with the electrical lead.

10. The lead retention and sealing apparatus, as set forth in claim 9, wherein the inner annular lip lies in a plane which is angled approximately 45° with respect to the longitudinal axis.

11. The lead retention and sealing system, as set forth in claim 10, wherein the base includes first and second inner peripheral surfaces, the first inner peripheral surface being nearer the closed end of the receiving channel than the second peripheral surface, the flexible annular ring member projecting inwardly toward the longitudinal axis from a location intermediate the first and second inner peripheral surfaces, the first inner peripheral surface having an inner extent which is greater than that of the second inner peripheral surface and wherein the area between the inner annular lip and the first inner peripheral surface defines the undercut region.

* * * * *